US00PP24619P2

(12) United States Plant Patent
Smith

(10) Patent No.: US PP24,619 P2
(45) Date of Patent: Jul. 8, 2014

(54) *CHRYSANTHEMUM* PLANT NAMED 'CIFZ0004'

(50) Latin Name: *Chrysanthemum×morifolium*
Varietal Denomination: CIFZ0004

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 31 days.

(21) Appl. No.: 13/694,372

(22) Filed: Nov. 27, 2012

(51) Int. Cl.
*A01H 5/00* (2006.01)

(52) U.S. Cl.
USPC ..... Plt./289

(58) Field of Classification Search
CPC ..... A01H 5/0255; A01H 5/025; A01H 5/02; A01H 5/00
USPC ..... Plt./289
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0004' particularly distinguished by the medium yellow decorative inflorescences, medium green foliage color, medium to large size rounded plant habit, with a natural season response of mid to late September.

1 Drawing Sheet

Latin name of the genus and species of the plant claimed: *Chrysanthemum×morifolium.*

Varietal denomination: 'CIFZ0004'.

BACKGROUND OF THE NEW PLANT

The present invention comprises a new *Chrysanthemum*, botanically known as *Chrysanthemum×morifolium*, and hereinafter referred to by the variety name 'CIFZ0004'.

'CIFZ0004' is a product of a planned breeding program. The new cultivar has medium yellow decorative inflorescences, medium green foliage color, medium to large size rounded plant habit, with a natural season response of mid to late September.

'CIFZ0004' originates as a whole plant mutation of a parent designated '05-M162A'. 'CIFZ0004' was discovered and selected by the inventor in November 2009 as a single flowering plant within a large population of the parent cultivar grown in pots outdoors in a controlled breeding program in Alva, Fla. The parent cultivar '05-M162A' has light lavender inflorescences.

The first act of asexual reproduction of 'CIFZ0004' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0004' are firmly fixed and are retained through successive generations of asexual reproduction.

'CIFZ0004' has not been observed under all possible environmental conditions. The phenotype may vary significantly with variations in environment such as temperature, light intensity, and day length.

Plant Breeder's Rights for this cultivar were applied for in Canada on Feb. 24, 2012 (12-7523) and at the Community Plant Variety Office on May 10, 2012 (2012-1023). 'CIFZ0004' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIFZ0004' with colors being as true as possible with an illustration of this type. The photographic drawing shows a flowering potted plant of the new variety, and a close-up of the inflorescence.

DETAILED BOTANICAL DESCRIPTION

The plant descriptions, measurements, and aforementioned photographs were taken in Gilroy, Calif. in early August 2012 outdoors. These plants were about 12-14 weeks of age grown in 1 gallon pots in an outdoor trial.

Color references are made to The Royal Horticultural Society Colour Chart (R.H.S.) 2001.

TABLE 1

DIFFERENCES BETWEEN THE NEW VARIETY 'CIFZ0004' AND A MOST SIMILAR VARIETY

| | 'CIFZ0004' | 'Golden Yohelga' (U.S. Plant Pat. No. 15,317) |
|---|---|---|
| Blackcloth flowering response: | Week faster | Week slower |
| Plant branch strength: | Greater | Weaker |
| Inflorescence color: | Lighter yellow shade | Somewhat darker shade |

Plant:

*Form, growth and habit.*—Herbaceous garden-type, stems upright and outwardly spreading, freely branching, strong and moderately vigorous growth habit.

*Plant height.*—22-25.0 cm.

*Plant height (inflorescence included).*—27-29.0 cm.

*Plant width.*—40-43.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Darker than RHS 137A.

*Immature, leaf color, lower surface.*—Closest to RHS 137B but little greyer.

*Mature, leaf color, upper surface.*—Darker than RHS 137A.

*Mature, leaf color, lower surface.*—Closest to RHS 137B but little greyer.

*Length.*—3.7-4.5 cm.

*Width.*—3.8-4.5 cm.

*Shape.*—Ovate.

*Base shape.*—Attenuate.

*Apex shape.*—Acute.

*Margin.*—Palmately lobed; irregularly incised.

*Texture, upper surface.*—Bifid T-shaped hairs.

*Texture, lower surface.*—Bifid T-shaped hairs.

*Color of veins, upper surface.*—RHS 144B.

*Color of veins, lower surface.*—RHS 144B.

*Pattern of veining.*—Palmate.

*Petiole color.*—RHS 144B.

*Length.*—1.1-1.4 cm.

*Diameter.*—0.2-0.3 cm.

*Texture.*—Bifid T-shaped hairs.

Stem:

*Quantity of main branches per plant.*—About 8.

*Color of stem.*—Closest but a bit darker than RHS 137A, and appears lighter due to the hairs.

*Length of stem.*—15-17.0 cm.

*Diameter.*—0.3 cm.

*Length of internodes.*—0.5-1.4 cm.

*Texture.*—Bifid T-shaped hairs.

*Color of peduncle.*—Closest to RHS 137A but appears lighter due to hairs.

*Length of peduncle.*—9-14.0 cm.

*Peduncle diameter.*—0.2 cm.

*Texture.*—Bifid T-shaped hairs.

Inflorescence:

*Type.*—Compositae, solitary decorative-type inflorescences borne terminally above foliage, ray florets arranged acropetally on a capitulum.

*Quantity of short days to flowering (response time).*—About 45-46 days.

*Natural season flowering.*—Mid to late September.

*Quantity of inflorescences per plant.*—75-85 plus about 100 buds in various stages.

*Lastingness of individual blooms on the plant.*—Somewhat more than 6 weeks from first color.

*Fragrance.*—Slightly spicy.

Bud (just when opening/showing color):

*Color.*—RHS 4C with RHS 13C apex.

*Length.*—0.7-1.0 cm.

*Width.*—0.9-1.0 cm.

*Shape.*—Oblate.

Immature inflorescence:

*Diameter.*—2.5-5.0 cm.

*Color of ray florets, upper surface.*—RHS 6D ground color, RHS 1C basally with RHS 9B apex.

*Color of ray florets, lower surface.*—RHS 8C.

Mature inflorescence:

*Diameter.*—5-6.0 cm.

*Depth.*—1.75-2.0 cm.

*Total diameter of disc.*—0.3-0.4 cm.

*Receptacle color.*—RHS 145C.

*Receptacle height.*—0.5 cm.

*Receptacle diameter.*—0.5 cm.

Ray florets:

*Average quantity of florets.*—145-165 in numerous whorls.

*Color of florets, upper surface.*—Closest to RHS 8B.

*Color of florets, lower surface.*—RHS 8C.

*Length.*—2.2-2.8 cm.

*Width.*—0.55-0.65 cm.

*Shape.*—Elliptical.

*Apex shape.*—Mostly praemorse.

*Base shape.*—Truncate.

*Margin.*—Entire.

*Texture, upper surface.*—Papillose.

*Texture, lower surface.*—Papillose.

Disc florets:

*Average quantity of florets.*—13-25.

*Color of florets.*—RHS 1C ground color with RHS 13A apex.

*Length.*—0.4-0.55 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—About 20.

*Color, upper surface.*—RHS 137C.

*Color, lower surface.*—RHS 137A.

*Length.*—0.8-0.9 cm.

*Width.*—0.2 cm.

*Shape.*—Lanceolate to linear.

*Apex shape.*—Acute.

*Base.*—Fused.

*Margins.*—Entire.

*Texture, upper surface.*—Glabrous.

*Texture, lower surface.*—Bifid T-shaped hairs.

Reproductive organs:

*Pistil.*—1, found on both types of florets.

*Length.*—0.5 cm.

*Style color.*—RHS 1C.

*Style length.*—0.45 cm.

*Stigma color.*—RHS 13A.

*Stigma shape.*—Bi-parted.

*Ovary color.*—Not developed enough at this date.

*Stamens.*—4, found only on the disc florets.

*Color of filaments.*—RHS 1C.

*Length filaments.*—0.1-0.15 cm.

*Anther color.*—RHS 17C.

*Anther length.*—0.05 cm.

*Anther shape*.—Oval.

*Color of pollen*.—RHS 17B.

*Pollen amount*.—Normal.

Fertility/seed set: Has not been observed to date.

Disease/pest resistance: Has not been observed to date.

What is claimed is:

1. A new and distinct variety of *Chrysanthemum* plant named 'CIFZ0004' substantially as illustrated and described herein.

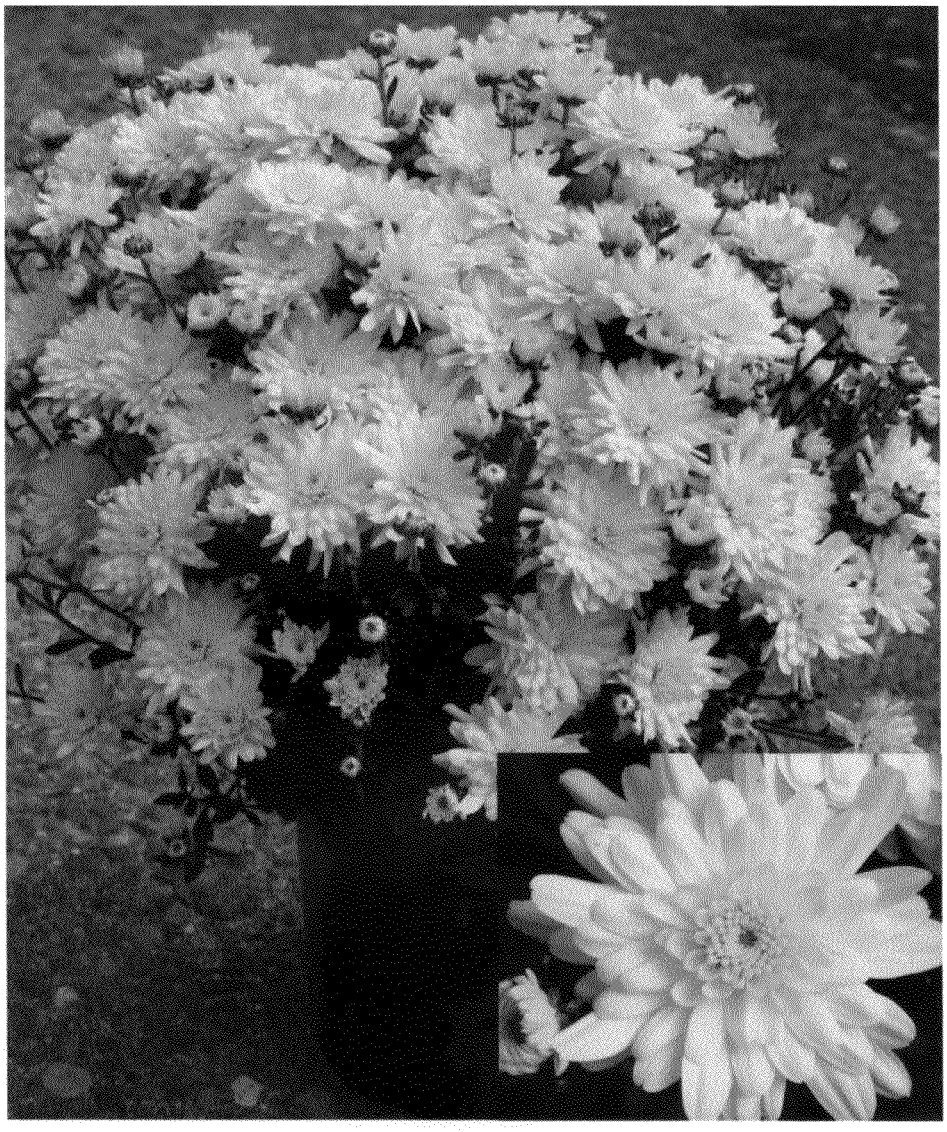

* * * * *